(12) United States Patent
Hockersmith et al.

(10) Patent No.: US 7,519,157 B2
(45) Date of Patent: Apr. 14, 2009

(54) SYSTEMS, METHODS AND APPARATUS FOR ATTACHMENT OF AN X-RAY TUBE TO AN X-RAY TUBE COLLIMATOR FRAME

(75) Inventors: Ron Kent Hockersmith, Waukesha, WI (US); Edward Emaci, Brookfield, WI (US); James Lorne Dodge, Waukesha, WI (US); Eric Matthew Plate, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 263 days.

(21) Appl. No.: 11/187,328

(22) Filed: Jul. 23, 2005

(65) Prior Publication Data
US 2007/0019783 A1    Jan. 25, 2007

(51) Int. Cl.
*H01J 35/02* (2006.01)
*G21K 1/02* (2006.01)

(52) U.S. Cl. .................. 378/121; 378/147; 378/197
(58) Field of Classification Search ............ 378/4, 378/11, 15, 21, 119, 121, 139, 140, 147, 378/160, 161, 193, 197, 204, 210
See application file for complete search history.

(56) References Cited

U.S. PATENT DOCUMENTS

| | | | | | |
|---|---|---|---|---|---|
| 2,998,526 | A | * | 8/1961 | Green et al. ............... | 378/147 |
| 4,464,778 | A | * | 8/1984 | Goldmann ................. | 378/150 |
| 4,799,245 | A | * | 1/1989 | Bernardi .................... | 378/15 |
| 4,880,985 | A | * | 11/1989 | Jones ..................... | 250/505.1 |
| 4,905,268 | A | * | 2/1990 | Mattson et al. ............ | 378/158 |
| 5,012,506 | A | * | 4/1991 | Span et al. ................. | 378/152 |
| 5,629,971 | A | * | 5/1997 | Jones et al. ................ | 378/145 |
| 5,712,889 | A | * | 1/1998 | Lanzara et al. ............. | 378/19 |
| 5,745,548 | A | * | 4/1998 | Dobbs et al. .............. | 378/207 |
| 6,246,742 | B1 | * | 6/2001 | Besson et al. ............... | 378/8 |
| 6,519,312 | B1 | * | 2/2003 | Tybinkowski et al. ......... | 378/4 |

* cited by examiner

*Primary Examiner*—Edward J Glick
*Assistant Examiner*—Thomas R Artman
(74) *Attorney, Agent, or Firm*—Peter Vogel, Esq.; William Baxter, Esq.; Michael G. Smith, Esq.

(57) ABSTRACT

Systems, methods and apparatus are provided through which in some embodiments, a wrap-around capture device of an X-ray collimator frame limits movement of an X-ray tube mounting bracket away from the X-ray collimator. In some embodiments, a C-shaped passive capture device is attached or mounted on the wrap-around capture device, having a portion that is positioned in between the wrap-around capture device and the X-ray collimator frame, which further limits movement of the X-ray tube mounting bracket.

24 Claims, 8 Drawing Sheets

SYSTEMS, METHODS AND APPARATUS FOR ATTACHMENT OF AN X-RAY TUBE TO AN X-RAY TUBE COLLIMATOR FRAME

FIELD OF THE INVENTION

This invention relates generally to X-ray tubes, and more particularly to attaching the X-ray tube to a collimator frame.

BACKGROUND OF THE INVENTION

Conventional X-ray tubes of computer tomography imaging systems are attached to a gantry. In some embodiments, the X-ray tube and gantry are attached through a number of bolts, typically four bolts.

The gantry rotates at velocities of more than three revolutions per second. The entire system apparatus for many systems weighs over one hundred kilograms. The rotation velocity and weight of the apparatus results in high centripetal accelerations.

Failure of the attachment could have a catastrophic effect on a person or other object in the path of the X-ray at the moment of failure of the attachment. Such potential failure and the effects have been contemplated and a realization has occurred that the potential catastrophic failure is to be avoided.

Some conventional systems require very complex gantries that are difficult to install.

For the reasons stated above, and for other reasons stated below which will become apparent to those skilled in the art upon reading and understanding the present specification, there is a need in the art for a failsafe attachment apparatus of an X-ray tube to other apparatus such as a gantry that does not require complex gantry.

BRIEF DESCRIPTION OF THE INVENTION

The above-mentioned shortcomings, disadvantages and problems are addressed herein, which will be understood by reading and studying the following specification.

In one aspect, an apparatus to provide reliable attachment of a medical X-ray imaging device such as an X-ray tube includes a collimator frame having a wrap-around capture mechanism and an X-ray tube operable to be mounted the collimator frame.

In another aspect, the wrap-around capture mechanism has an L-shape in which an appendage of the wrap-around capture mechanism extends over the X-ray tube.

In yet another aspect, the wrap-around capture mechanism further is formed integrally as a portion of the collimator frame.

In still another aspect, the apparatus includes a passive capture device that is operable to be mounted to the wrap-around capture mechanism, in which at least a portion of the passive capture device is positioned between the wrap-around capture mechanism and the X-ray tube.

In a further aspect, the passive capture device has a C "shape."

In yet a further aspect, a method of attaching an X-ray tube to a rotatable gantry of a computed tomography imaging system includes positioning a mounting bracket of X-ray tube casing along an X axis of an X-ray collimator frame of the gantry, placing an interposer plate into a channel formed in a surface of the mounting bracket; moving the mounting bracket and the collimator frame into contact and tightening bolts between the mounting bracket and the and the collimator frame.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into four sections. In the first section, a system level overview is described. In the second section, embodiments of apparatus are described. In the third section, embodiments of methods are described. Finally, in the fourth section, a conclusion of the detailed description is provided.

System Level Overview

Figure 1:
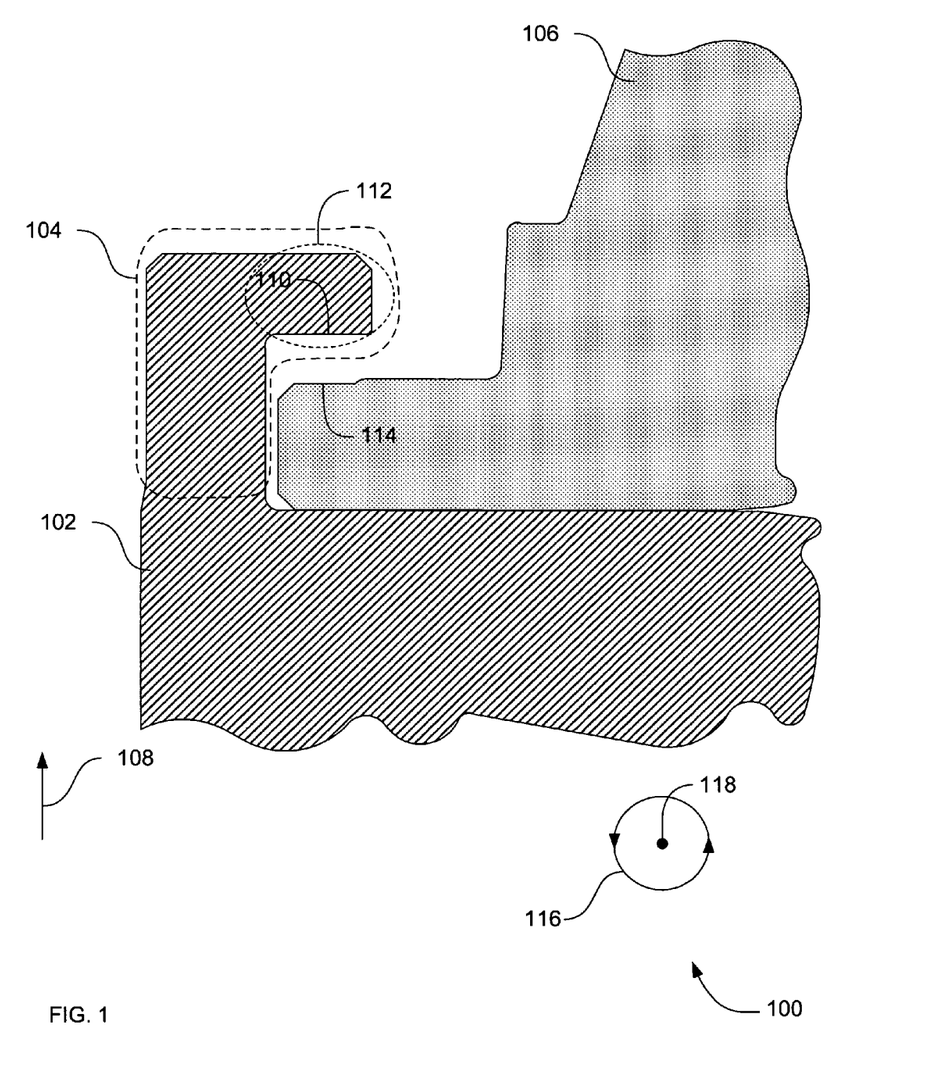
FIG. 1 is a block diagram of a cross section of an overview of a system to provide more reliable attachment of an X-ray tube.

FIG. 1 is a block diagram of a cross section of an overview of a system 100 to provide more reliable attachment of an X-ray tube. System 100 solves the need in the art for a more safe attachment of the medical imaging device 106 such as an X-ray tube.

System 100 includes a collimator frame 102. The collimator frame 102 has or includes a wrap-around capture mechanism 104. The collimator frame 102 also includes cams and motors which are not shown and which direct an X-ray beam. System 100 also includes a medical imaging device 106 that is operable to be mounted the collimator frame 102.

The wrap-around capture mechanism 104 keeps the medical imaging device 106 in proximity to the collimator frame 102 when the mounting of medical imaging device 106 to the collimator frame 102 fails and when a force 108 urges the collimator frame 102 away from the medical imaging device 106. More specifically, a surface 110 of a wrap-around appendage 112 of the collimator frame 102 is about parallel with an opposing surface 114 of the medical imaging device 106. Surfaces 110 and 114 are about perpendicular to force 108. Force 108 will cause the collimator frame 102 and the medical imaging device 106 to move in opposite directions relative to each other. In some embodiments, the force 108 is a centripetal force created by rotation 116 of system 100 about an axis 118 that is positioned on the opposite side of the collimator frame 102 from the medical imaging device 106.

If enough relative movement occurs of the medical imaging device 106 and collimator frame 102, the two parallel surfaces 110 and 114 meet, and the movement of the collimator frame 102 and the medical imaging device 106 proceeds no further. So, for any other means (not shown) of attaching the medical imaging device 106 to the collimator frame 102, the imaging device will move in opposite directions in accordance with force 108 no more than the extent of the distance between surfaces 110 and 114. Thus system 100 solves the need in the art for a more safe attachment of the medical imaging device 106 such as an X-ray tube.

System 100 provides an additional level of safety, with little interaction required by a field service engineer or field installer or a complex gantry. The wrap around design effectively captures the medical imaging device 106 in the event that a primary attachment mechanism fails.

De minimus interaction is required by a field service engineer to install the wrap-around capture mechanism 104 when installing a new medical imaging device 106. The medical imaging device 106 can be installed in any conventional fashion, with minimal change compared to a non-fail safe design. A primary attachment mechanism is left unchanged and unaffected. System 100 provides a safe attachment mechanism that can be installed on systems retroactively.

System 100 shows an embodiment of the wrap-around capture mechanism 104 that has an L-shape in which an appendage of the wrap-around capture mechanism (the wrap-around appendage 112) extends over a portion of the medical imaging device 106. The appendage 112 of the collimator frame 102 is also known as a "finger."

System 100 also shows an embodiment in which the wrap-around capture mechanism 104 is formed integrally as a portion of the collimator frame 102. In other embodiments, the wrap-around capture mechanism 104 is a portion that is manufactured separately from the collimator frame 102 and the wrap-around capture mechanism 104 mounted or attached to the collimator frame 102.

While the system 100 is not limited to any particular collimator frame 102, wrap-around capture mechanism 104, medical imaging device 106, force 108, collimator frame surface 110, wrap-around appendage 112 and opposing surface 114 for sake of clarity a simplified collimator frame 102, wrap-around capture mechanism 104, medical imaging device 106, force 108, collimator frame surface 110, wrap-around appendage 112 and medical imaging device opposing surface 114 are described. In some embodiments, the portion of the medical imaging device 106 or X-ray tube shown in FIG. 1 is an X-ray tube mounting bracket.

Apparatus Embodiments

In the previous section, a system level overview of the operation of an embodiment was described. In this section, the particular apparatus of such an embodiment are described.

Figure 2:
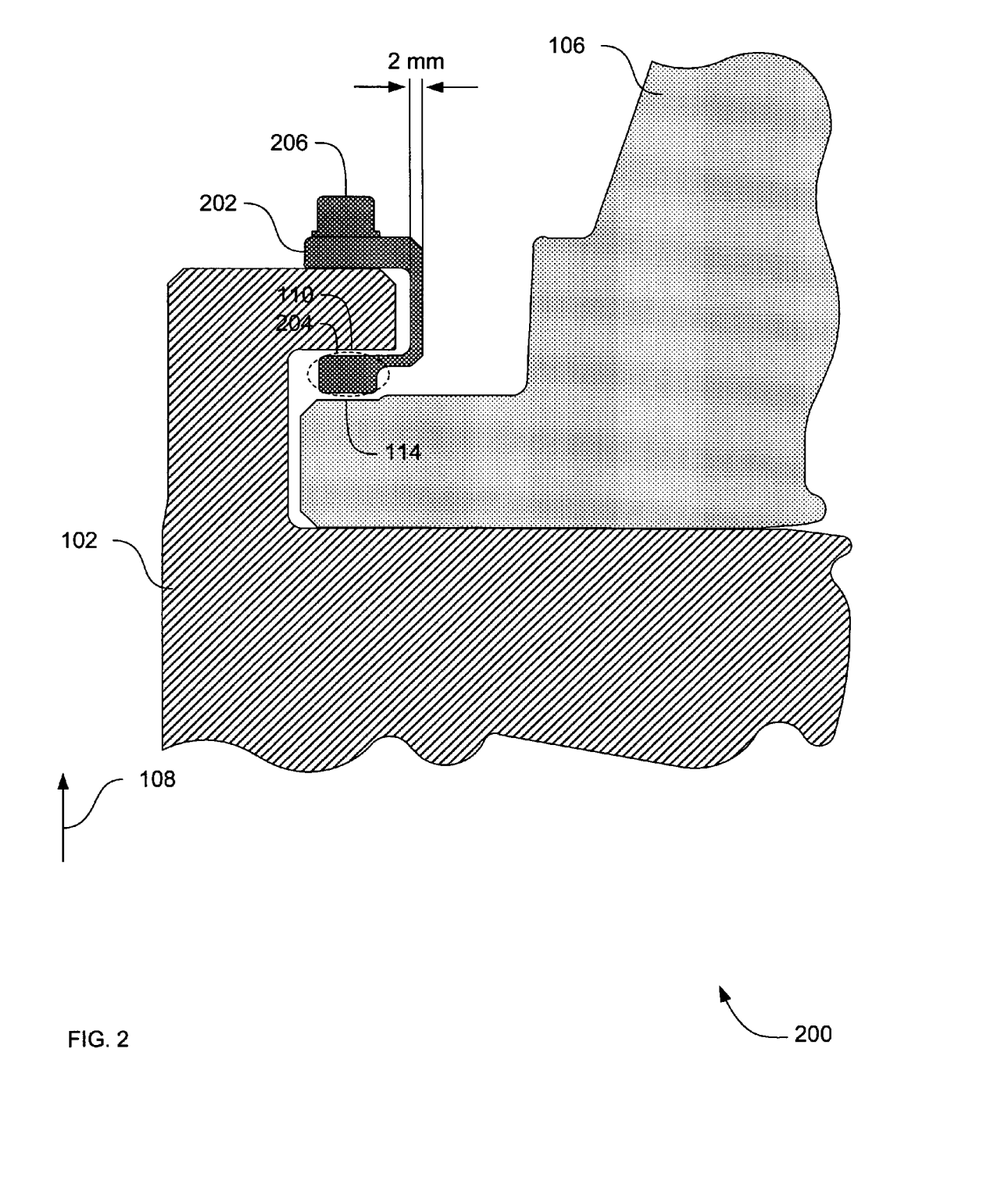
FIG. 2 is a diagram of apparatus to provide more reliable attachment of an X-ray tube, the apparatus having a passive capture device according to an embodiment.

FIG. 2 is a diagram of apparatus 200 to provide more reliable attachment of an X-ray tube, the apparatus having a passive capture device according to an embodiment. Apparatus 200 solves the need in the art for a more safe attachment of the medical imaging device 106 such as an X-ray tube.

Apparatus 200 includes a passive capture device 202. Most notably the passive capture device 202 includes a portion 204 that is positioned between the surface 110 of the wrap-around appendage 112 of the collimator frame 102 and the opposing surface 114 of the medical imaging device 106. The portion 204 reduces and limits the amount of distance that the collimator frame 102 and the medical imaging device 106 move in opposite directions relative to each other under the urging of force 108 until the two parallel surfaces 110 and 114 meet, and the movement of the collimator frame 102 and the medical imaging device 106 proceeds no further. More simply, the portion 204 takes up a portion of the space between the surfaces 110 and 114, thus limiting and reducing the amount of distance that the collimator frame 102 and the medical imaging device 106 move in opposite directions relative to each other under the urging of force 108.

If enough movement of the collimator frame 102 and the medical imaging device 106 occurs, the two parallel surfaces 110 and 114 meet, and the movement of the collimator frame 102 and the medical imaging device 106 proceeds no further. So, when any other means (not shown) of attaching the medical imaging device 106 to the collimator frame 102, the imaging device will move in opposite relative directions in accordance with force 108 no more than the sum of the extent of the distance between surface 110 and portion 204 and the extent of the distance between 114 and portion 204. Thus apparatus 200 solves the need in the art for a more safe attachment of the medical imaging device 106 such as an X-ray tube.

The embodiment of the passive capture device 202 shown in FIG. 2 is also known as a "C-spacer" because of the "C" shape of the passive capture device 202. Other embodiments of the passive capture device 202 are not necessarily C-shaped.

In the embodiment of the apparatus 200 shown in FIG. 2, the sum of the distance between surfaces 110 and 114 is about 2 millimeters (mm) greater than the width of the portion 204. In some further embodiments, the distance between surface 110 and the portion 204 is about 1 mm and the distance between the surface 114 and the portion 204 is also about 1 mm.

In the embodiment of the apparatus 200 shown in FIG. 2, the width of the middle portion of the passive capture device 202 is about 2 mm. When the medical imaging device 106 and the collimator frame 102 move in opposing directions, surface 114 of the medical imaging device 106 will first meet the portion 204 of the passive capture device 202. With the application of a greater extent of force 108, the middle portion of the passive capture device 202 will flex and bend until the surface 110 of the collimator frame 102 meets the portion 204 of the passive capture device 202, thus preventing any further movement of the medical imaging device 106 relative to the collimator frame 102.

The passive capture device 202 is attached, mounted or fixed to the wrap-around capture mechanism 104. In the embodiment shown in FIG. 2, the passive capture device 202 is attached, mounted or fixed to the wrap-around capture mechanism 104 by means of a bolt 206 that passes through the passive capture device 202 and into the wrap-around capture mechanism 104. In some embodiments, bolt 206 is a plurality of bolts. In some embodiments, bolt 206 is a M6 bolt. Other means of attachment of the passive capture device 202 to the wrap-around capture mechanism 104 include clamps, pins, or a dovetail type design.

The passive capture device 202 reduces impact loads caused by release of the medical imaging device 106 while spinning at high speed, in addition to limiting travel of the medical imaging device 106 in such an event. The passive capture device 202 also provides a "lock", since once the passive capture device 202 is installed the medical imaging device 106 is trapped and cannot move more than 3 mm in any direction and only 0.4 mm radially outward. This limited movement provides restraint during gantry tilt conditions and severe vibratory environments. The passive capture device 202 can be designed with a specific stiffness that allows the passive capture device 202 to deform just enough to allow a load to be transferred to the wrap-around capture mechanism 104, before overloading the primary attachment mechanism which attach wrap-around capture mechanism 104 to the collimator frame. Apparatus 200 can be implemented by changing two major components, the collimator frame 102 and the medical imaging device 106.

Figure 3:
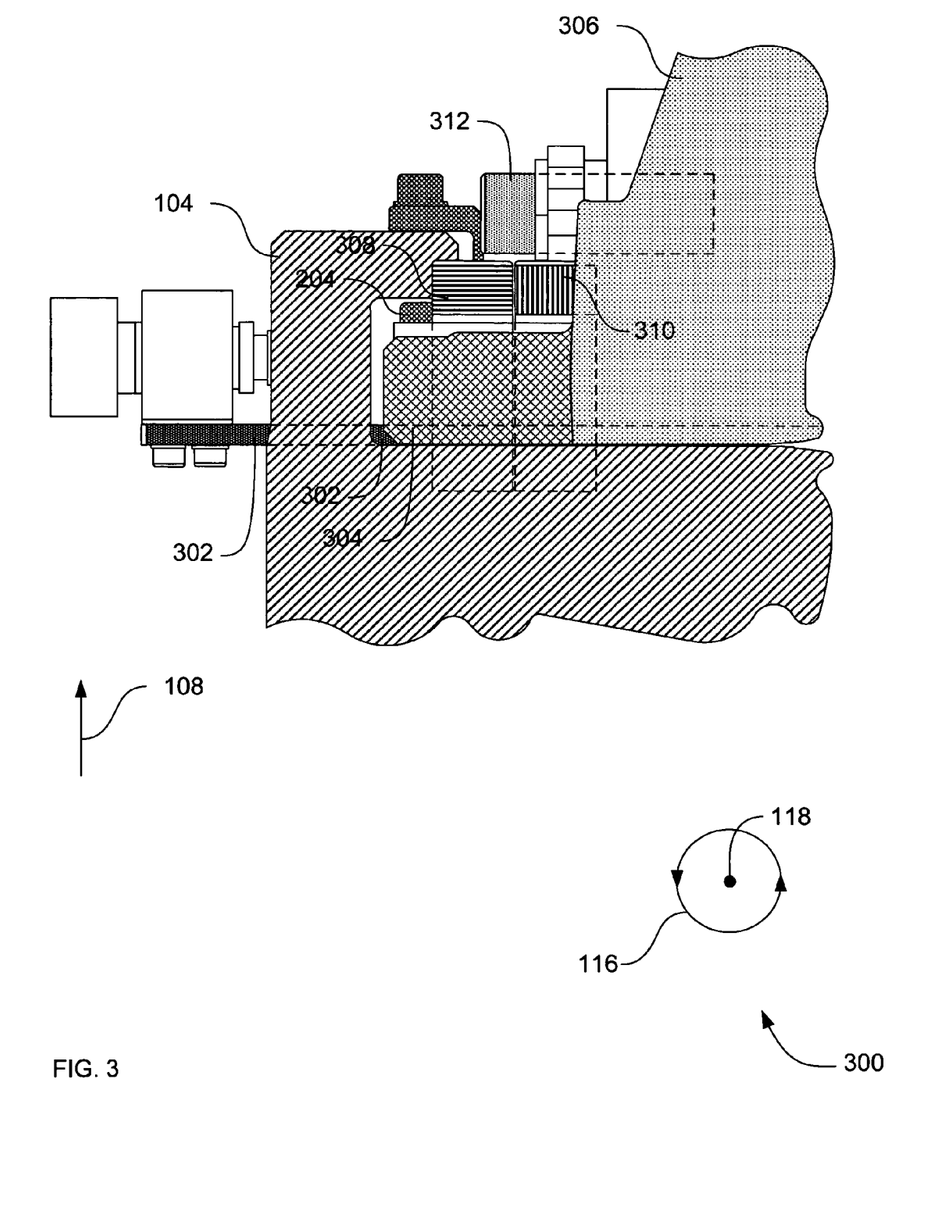
FIG. 3 is a diagram of apparatus to provide more reliable attachment of an X-ray tube, the apparatus having a passive capture device and an interposer plate according to an embodiment.

FIG. 3 is a diagram of apparatus 300 to provide more reliable attachment of an X-ray tube, the apparatus having a passive capture device and an interposer plate according to an embodiment. Apparatus 300 solves the need in the art for a more safe attachment of an X-ray tube.

Apparatus 300 includes an interposer plate 302 that extends through the collimator frame 102 into channels (not shown) formed into an X-ray tube mounting bracket 304 of an X-ray tube 306. The interposer plate 302 prevents fore and aft movement of the X-ray tube mounting bracket 304 along an X axis and movement along a Z axis.

Apparatus 300 also include two bolts, 308 and 310 that attaches the collimator frame 102 and the X-ray tube mounting bracket 304. Apparatus also includes a bolt 312 that attaches the mounting bracket 304 and the X-ray tube 306.

In some embodiments, where the relative dimension of parts of apparatus 300 are within certain proportions, the interposer plate 302 will nearly eliminate any relative fore and aft movement of the collimator frame 102 and the X-ray tube mounting bracket 304. When the sum of the distance between surfaces 110 and 114 minus the width of the portion 204 is less than the thickness of the interposer plate 302, any fore and aft movement of the collimator frame 102 and the X-ray tube mounting bracket 304 is limited to approximately the amount of manufacturing tolerances between the interposer plate 302 and the channel. For example, when the sum of the distance between surfaces 110 and 114 minus the width of the portion 204 is 2 mm and the thickness of the interposer plate 302 is greater than 2 mm, the movement of the collimator frame 102 and the X-ray tube mounting bracket 304 away from each other is limited to about 2 mm. In other embodiments, movement of the collimator frame 102 and the X-ray tube mounting bracket 304 away from each other is limited to about 0.4 mm. Yet, within that range of movement, the interposer plate 302 will prevent any significant fore and aft movement of the movement of the collimator frame 102 and the X-ray tube mounting bracket 304. The movement of the collimator frame 102 and the X-ray tube mounting bracket 304 would have to move more than 2 mm away from each other in order to be free and clear in fore and aft movement.

Figure 4:
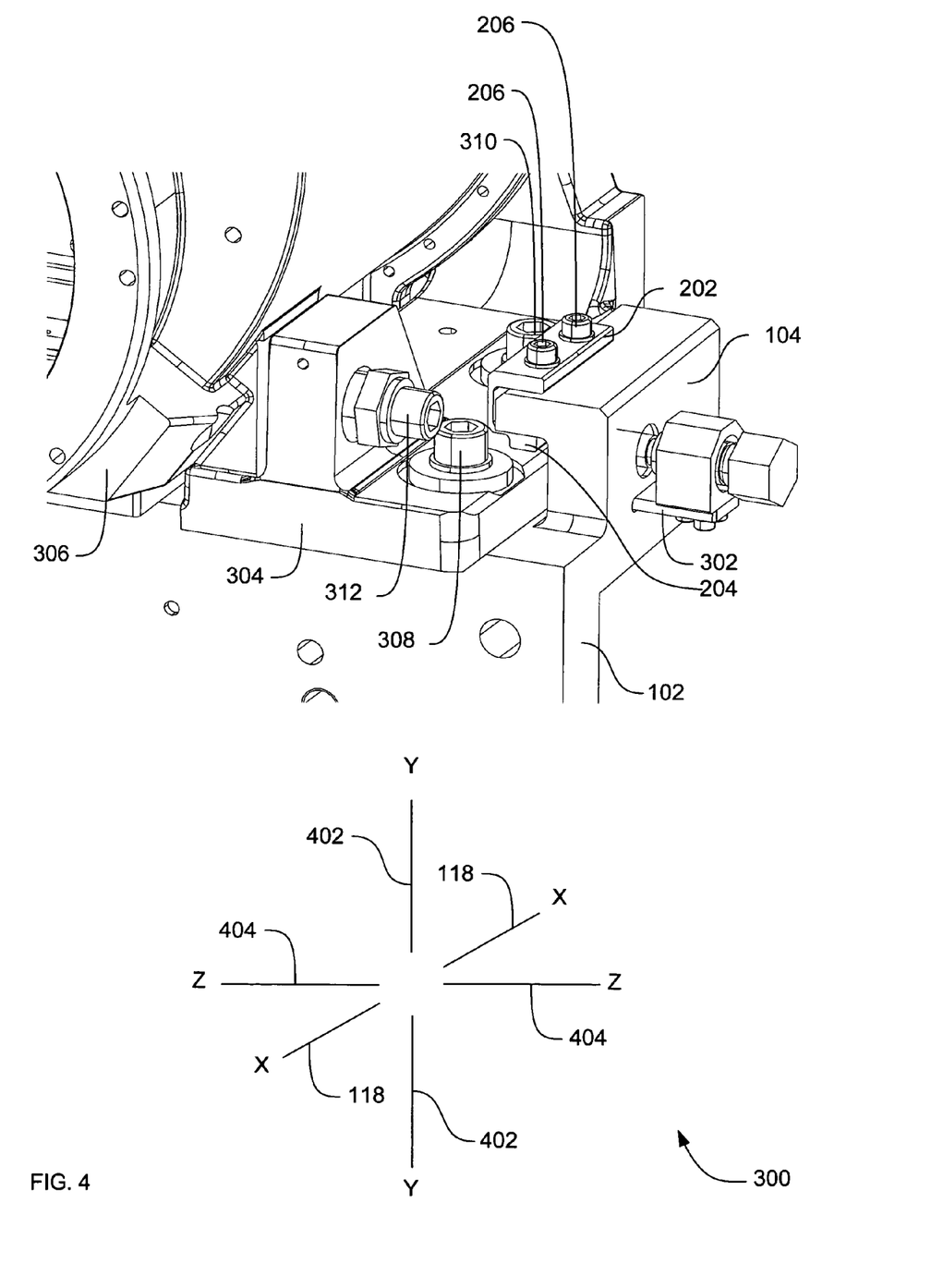
FIG. 4 is a back-side close-up view isometric diagram of the apparatus in FIG. 3.

FIG. 4 is a back-side close-up view isometric diagram of apparatus 300 according to an embodiment. Apparatus 300 solves the need in the art for a more safe attachment of an X-ray tube.

In FIG. 4, apparatus 300 includes a collimator frame 102, a wrap-around capture mechanism 104, a passive capture device 202, a portion 204 of the passive capture device 202, a bolt 206, an interposer plate 302, an X-ray tube mounting bracket 304, an X-ray tube 306, and bolts 308, 310 and 312.

The wrap-around capture mechanism 104 restrains movement of the X-ray tube mounting bracket 304 and the X-ray tube 306 in a Y-axis 402. The interposer plate 302 restrains movement of the X-ray tube mounting bracket 304 and the X-ray tube 306 in the Z-axis 404 and the X-axis 118. The interposer plate 302 prevents fore and aft movement along the axis X 118 and the Z axis of the X-ray tube mounting bracket 304.

Figure 5:
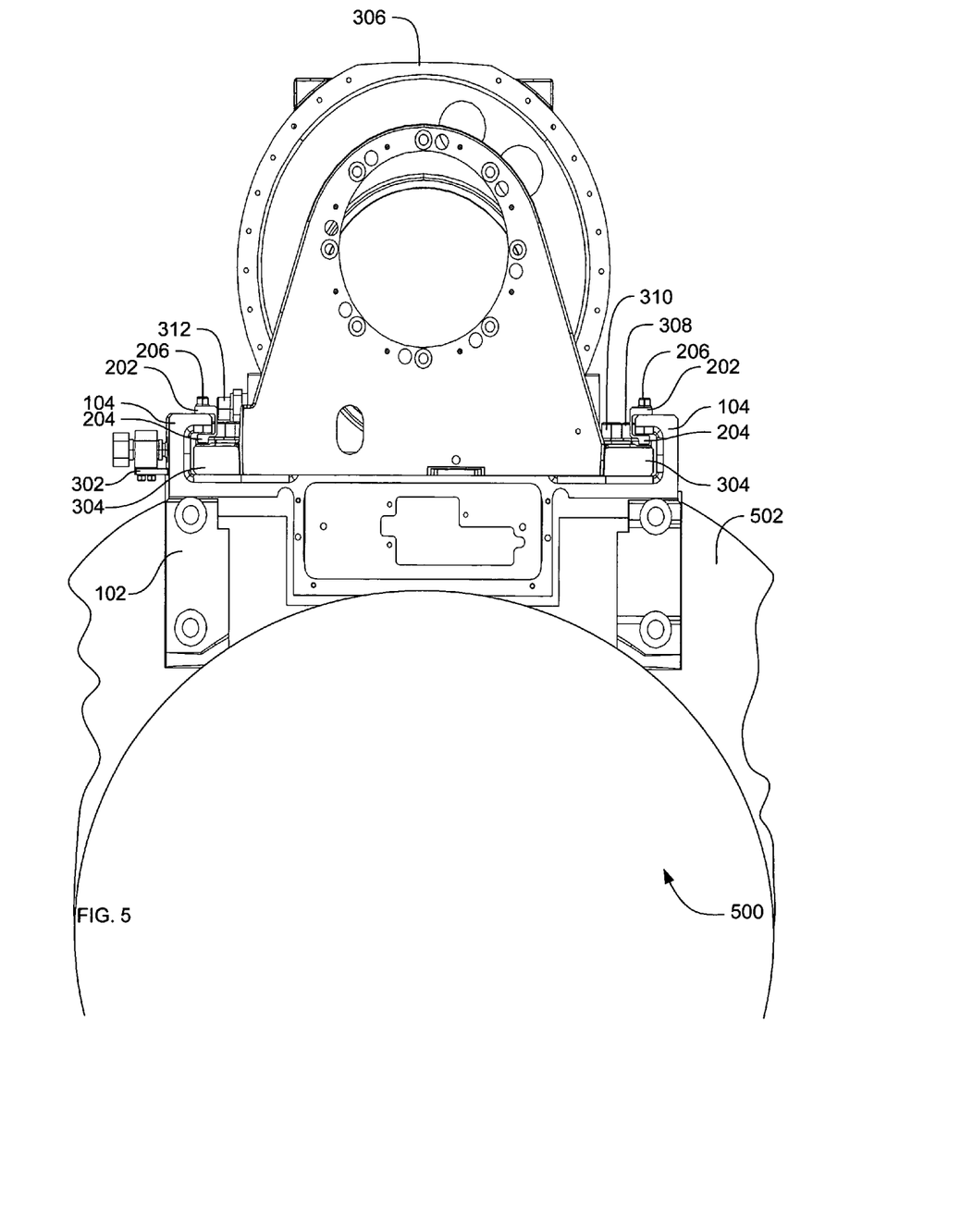
FIG. 5 is a front-side full-view diagram of the apparatus in FIG. 3 including a gantry.

FIG. 5 is a front-side full-view diagram of apparatus 300 including a gantry according to an embodiment. Apparatus 500 solves the need in the art for a more safe attachment of an X-ray tube.

In FIG. 5, apparatus 500 includes a collimator frame 102, a wrap-around capture mechanism 104, a passive capture device 202, a portion 204 of the passive capture device 202, a bolt 206, an interposer plate 302, an X-ray tube mounting bracket 304, an X-ray tube 306, and bolts 308, 310 and 312.

Apparatus 500 also includes a gantry 502. The gantry 502 is a cylindrically shaped object that supports or is operably coupled, attached or mounted to the collimator frame 102 at four points.

Figure 6:
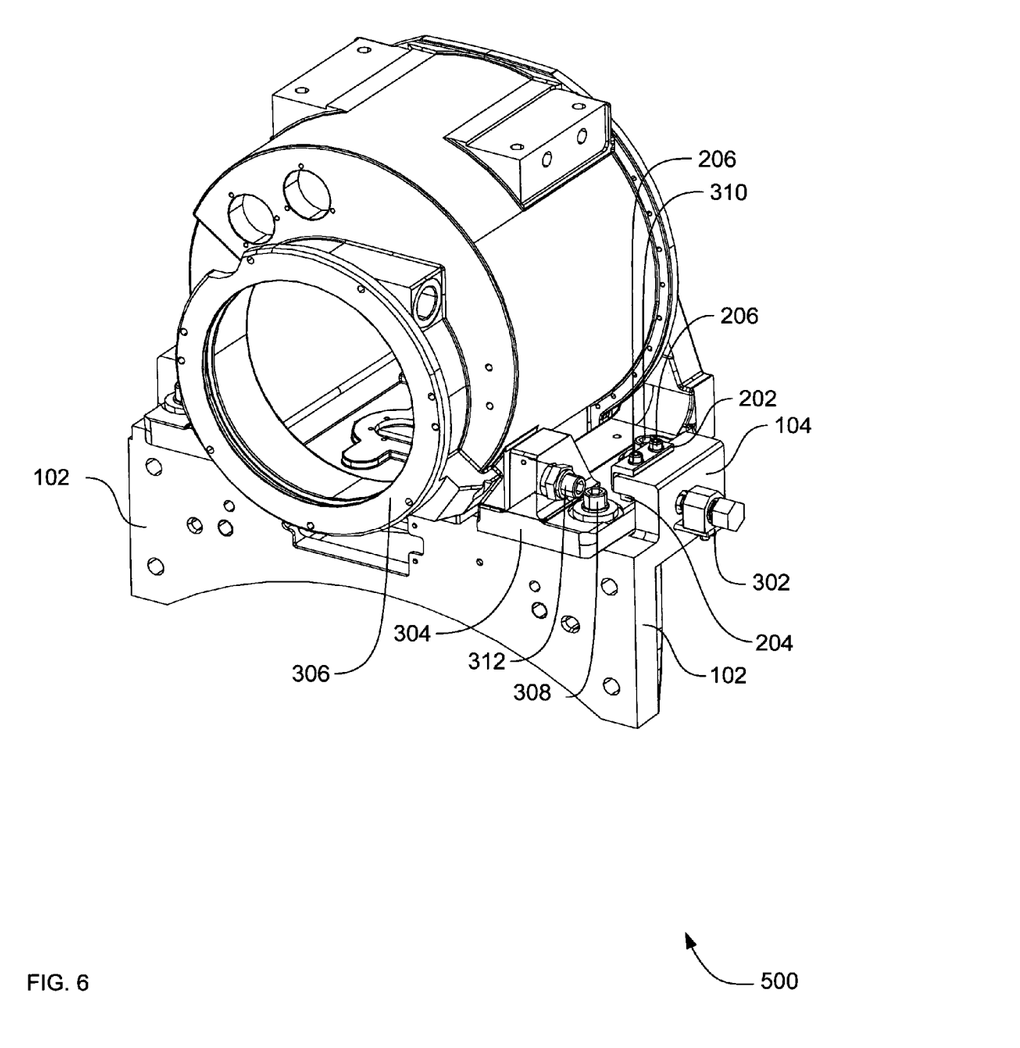
FIG. 6 is a back-side view-full isometric diagram of the apparatus in FIG. 3.

FIG. 6 is a back-side view-full isometric diagram of apparatus 300 according to an embodiment. Apparatus 500 solves the need in the art for a more safe attachment of an X-ray tube.

In FIG. 6, apparatus 300 includes the collimator frame 102, the wrap-around capture mechanism 104, the passive capture device 202, the portion 204 of the passive capture device 202, the bolt 206, the interposer plate 302, the X-ray tube mounting bracket 304, and the X-ray tube 306, bolts 308, 310 and 312.

Figure 7:
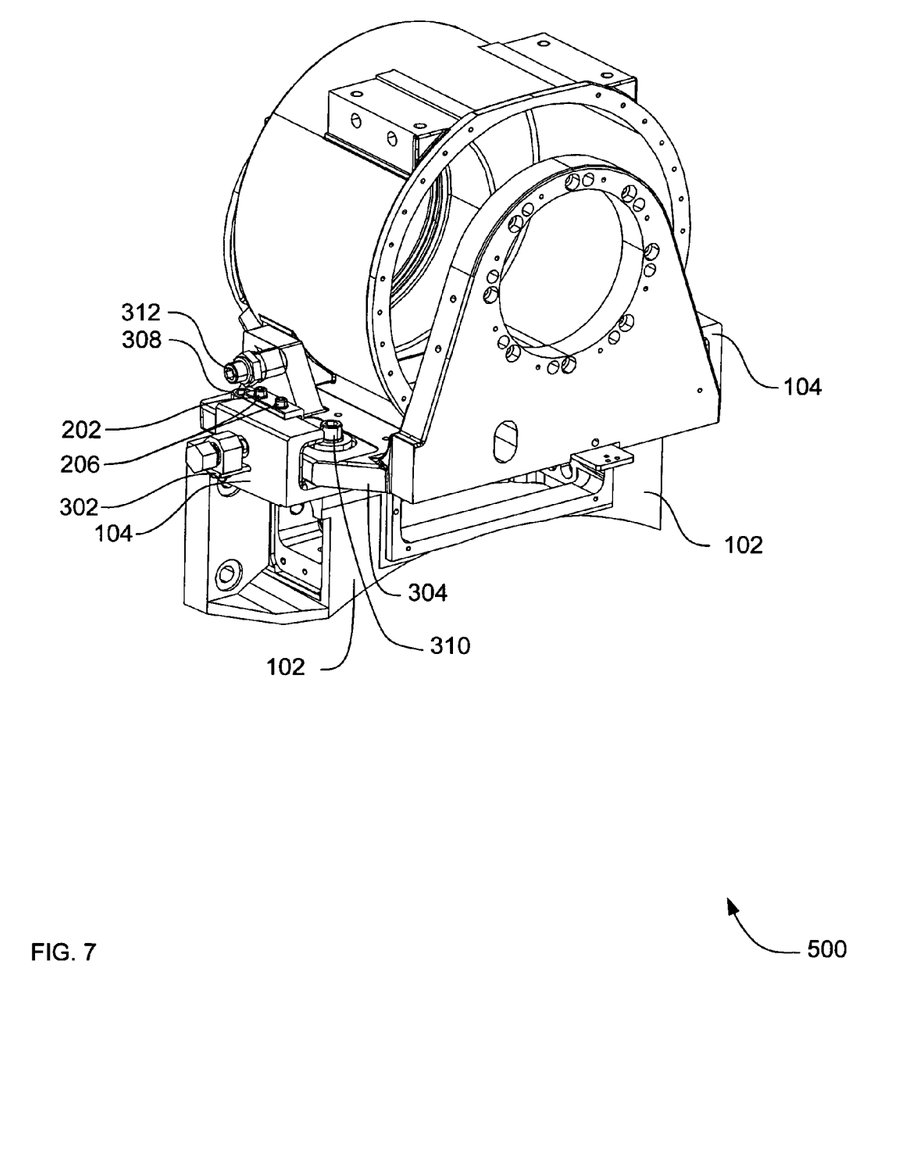
FIG. 7 is a front-side full-view diagram of the apparatus in FIG. 3.

FIG. 7 is a front-side full-view diagram of apparatus 300 according to an embodiment. Apparatus 300 solves the need in the art for a more safe attachment of an X-ray tube.

In FIG. 7, apparatus 300 includes the collimator frame 102, the wrap-around capture mechanism 104, the passive capture device 202, the bolt 206, the interposer plate 302, and the X-ray tube mounting bracket 304, bolts 308, 310 and 312.

Method Embodiments

In the previous section, apparatus of the operation of an embodiment was described. In this section, the particular methods of such an embodiment are described by reference to a flowchart.

Figure 8:
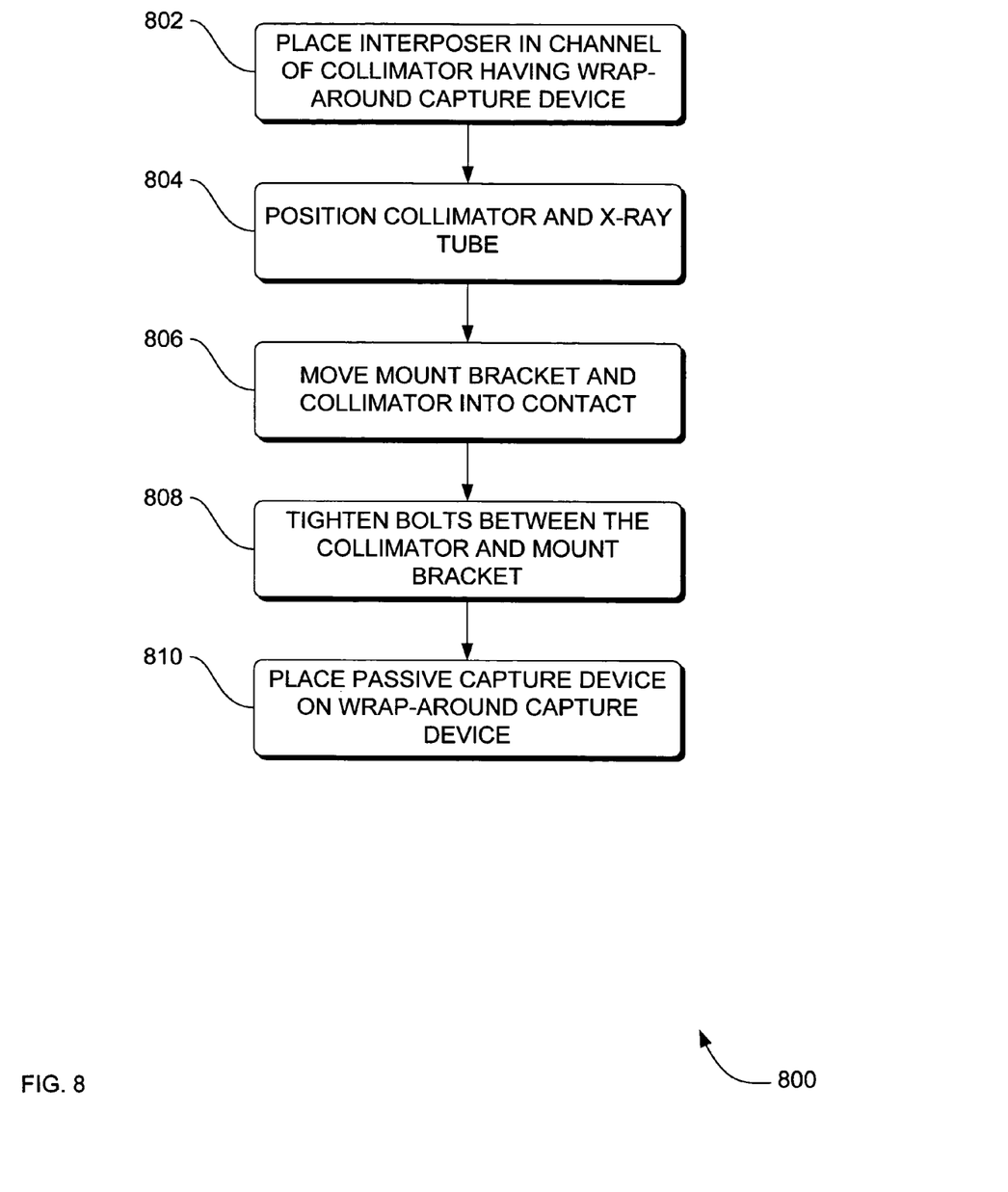
FIG. 8 is a flowchart of a method to attach an X-ray tube to a rotatable gantry of a computed tomography imaging system according to an embodiment.

FIG. 8 is a flowchart of a method 800 to attach an X-ray tube to a rotatable gantry of a computed tomography imaging system according to an embodiment. Method 800 solves the need in the art to provide a safer attachment of the X-ray tube.

Method 800 includes placing 802 an interposer plate 302 into a channel formed in a surface of a collimator frame 102 of a casing 306 of the X-ray tube. The collimator frame 102 has a wrap-around capture mechanism 104.

Thereafter, method 800 also includes positioning 804 the casing 306 of the X-ray tube along an X axis 118. The X-ray tube casing 306 has a mounting bracket 304. Some embodiments of the positioning include sliding the mounting bracket under the wrap-around capture mechanism. An interposer plate is preassembled on the collimator frame 102. When the tube is placed into the wrap around capture, the interposer is already in the channel in the bottom of the tube mounting bracket.

Subsequently, method 800 includes moving 806 the X-ray tube casing and the gantry 502 into contact and tightening 808 bolts between the gantry 502 and the mounting bracket 304.

In some embodiments, method 800 subsequently includes placing 810 a passive capture device 202 on the wrap-around capture mechanism 104. In some embodiment the placing 810 is performed after alignment of a focal spot of the X-ray tube.

CONCLUSION

An attachment apparatus between an X-ray tube and a rotatable gantry is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. One of ordinary skill in the art will appreciate that implementations can be made in other embodiments that provide the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future gantries, X-ray tubes, collimator frames and X-ray tube mounting brackets.

The terminology used in this application is meant to include all environments and alternate technologies which provide the same functionality as described herein.

We claim:

1. An apparatus to provide reliable attachment of an X-ray tube, the apparatus comprising:
    a collimator frame having a wrap-around capture mechanism, the wrap-around capture mechanism and the collimator frame formed as one piece from the same material; and
    an X-ray tube operably mounted to the collimator frame.

2. The apparatus of claim 1, wherein the wrap-around capture mechanism further comprises:
    an L-shaped wrap-around capture mechanism in which an appendage of the wrap-around capture mechanism extends over the X-ray tube.

3. The apparatus of claim 1, wherein the apparatus further comprises:
    a passive capture device mounted to the wrap-around capture mechanism, wherein at least a portion of the passive capture device is positioned between the wrap-around capture mechanism and the X-ray tube.

4. The apparatus of claim 3, wherein the passive capture device further comprises:
    a C-shaped passive capture device.

5. The apparatus of claim 1, wherein the X-ray tube further comprises:
    an X-ray tube mounting bracket mounted to the collimator frame; and
    an X-ray tube casing mounted to the X-ray tube mounting bracket.

6. The apparatus of claim 5, wherein the wrap-around capture mechanism further comprises:
    a L-shape in which an appendage of the wrap-around capture mechanism extends over the X-ray tube mounting bracket.

7. The apparatus of claim 5, wherein the X-ray tube mounting bracket further comprises a channel formed into a surface of the X-ray tube mounting bracket wherein the X-ray tube casing further comprises a channel formed into a surface of the X-ray tube casing, and wherein the apparatus further comprises:
    an interposer plate that fits into the channel of the X-ray tube mounting bracket and that fits into the channel of the X-ray tube casing.

8. The apparatus of claim 1, wherein the X-ray tube mounting bracket is mounted to the collimator frame by a plurality of bolts.

9. The apparatus of claim 1, wherein the apparatus further comprises:
    a medical imaging apparatus.

10. A collimator comprising:
    an X-ray collimator frame;
    a wrap-around capture mechanism operably coupled to the X-ray collimator frame;
    a gantry operably coupled to the X-ray collimator frame;
    an X-ray tube mounting bracket mounted to the X-ray collimator frame by a plurality of bolts; and
    an X-ray tube casing mounted to the X-ray tube mounting bracket, and
    a passive capture device mounted to the wrap-around capture mechanism, wherein at least a portion of the passive capture device is positioned between the wrap-around capture mechanism and the X-ray tube mounting bracket,
    wherein the passive capture device further comprises a C-shaped passive capture device.

11. The collimator of claim 10, wherein the wrap-around capture mechanism further comprises:
    a wrap-around capture mechanism formed integrally as a portion of the collimator.

12. The collimator of claim 10, wherein the X-ray collimator further comprises:
    a medical X-ray collimator frame.

13. The collimator of claim 10, wherein the passive capture device includes a portion that is positioned between a surface of the wrap-around capture mechanism and an opposing surface of the X-ray tube mounting bracket.

14. The collimator of claim 13, wherein the wrap-around capture mechanism further comprises:
    an L-shaped wrap-around capture mechanism in which an appendage of the wrap-around capture mechanism extends over the X-ray tube mounting bracket.

15. The collimator of claim 14, wherein a surface of the appendage is about parallel with an opposing surface of the X-ray tube mounting bracket.

16. The collimator of claim 15, wherein movement between the X-ray tube mounting bracket and the collimator frame, the two parallel surfaces meet, and the movement between the X-ray tube mounting bracket and the collimator frame proceeds no further.

17. The collimator of claim 13, wherein the X-ray tube mounting bracket further comprises a channel formed into a surface of the X-ray tube mounting bracket wherein the X-ray tube casing further comprises a channel formed into a surface of the X-ray tube casing, and wherein the apparatus further comprises:
    an interposer plate that fits into the channel of the X-ray tube mounting bracket and that fits into the channel of the X-ray tube casing.

18. A computer tomography imaging system comprising:
    a medical X-ray tube casing;
    an X-ray tube mounting bracket operably coupled to the medical X-ray tube casing;
    an X-ray collimator frame having a wrap-around capture mechanism, the wrap-around capture mechanism having an L-shape in which a portion of the L-shape extends over the X-ray tube mounting bracket, the wrap-around capture mechanism formed integrally as a portion of the X-ray collimator frame;
    a gantry operably coupled to the X-ray collimator frame; and a C-shaped passive capture device operably coupled to the wrap-around capture mechanism, wherein at least a portion of the C-shaped passive capture device is positioned between the wrap-around capture mechanism and the X-ray tube mounting bracket.

19. The computer tomography imaging system of claim 18, wherein the passive capture device includes a portion that is positioned between a surface of the wrap-around capture mechanism and an opposing surface of the X-ray tube mounting bracket.

20. The computer tomography imaging system of claim 19, wherein the portion takes up a portion of the space between the surfaces and the opposing surface, thus limiting and reducing the amount of distance that the X-ray collimator frame and the medical X-ray tube casing move in opposite directions relative to each other under an urging of a force.

21. The computer tomography imaging system of claim 18, wherein the X-ray tube mounting bracket further comprises a channel formed into a surface of the X-ray tube mounting bracket and wherein the X-ray tube casing further comprises a channel formed into a surface of the X-ray tube casing, and wherein the computer tomography imaging system further comprises:
   an interposer plate that fits into the channel of the X-ray tube mounting bracket and that fits into the channel of the X-ray tube casing.

22. A method to attach an X-ray tube to a rotatable gantry comprising:
   placing an interposer plate into a channel formed in a surface of the X-ray tube collimator frame, the X-ray tube collimator frame operably coupled to the rotable gantry, the X-ray tube collimator frame further comprising a wrap-around capture mechanism;
   positioning an X-ray tube along an X axis, the X-ray tube having a mounting bracket;
   moving the X-ray tube and the rotatable gantry into contact;
   tightening bolts between the rotatable gantry and the mounting bracket; and
   placing a passive capture device on the wrap-around capture mechanism.

23. The method of claim 22, wherein the positioning further comprises:
   sliding the mounting bracket under the wrap-around capture mechanism.

24. An apparatus comprising:
   an interposer plate placed into a channel formed in a surface of the X-ray tube collimator frame, the X-ray tube collimator frame operably coupled to a rotable gantry, the X-ray tube collimator frame further comprising a wrap-around capture mechanism; an X-ray tube positioned along an X axis of the apparatus, the X-ray tube having a mounting bracket;
   the X-ray tube in contact with the rotatable gantry;
   bolts attaching the rotatable gantry to the mounting bracket; and
   a passive capture device placed on the wrap-around capture mechanism.

* * * * *